United States Patent
Shinkawa et al.

(10) Patent No.: US 9,567,563 B2
(45) Date of Patent: Feb. 14, 2017

(54) ASPERGILLUS MUTANT STRAIN AND TRANSFORMANT THEREOF

(71) Applicant: HONDA MOTOR CO., LTD., Tokyo (JP)

(72) Inventors: Satoru Shinkawa, Saitama (JP); Shigenobu Mitsuzawa, Saitama (JP); Maiko Tanaka, Saitama (JP); Tomohiro Imai, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 15/014,585

(22) Filed: Feb. 3, 2016

(65) Prior Publication Data
US 2016/0230140 A1    Aug. 11, 2016

(30) Foreign Application Priority Data
Feb. 5, 2015   (JP) ................. 2015-021497

(51) Int. Cl.
| | |
|---|---|
| C12N 1/15 | (2006.01) |
| C12N 1/14 | (2006.01) |
| C07K 14/38 | (2006.01) |
| C12N 9/24 | (2006.01) |
| C12N 9/48 | (2006.01) |
| C12N 9/62 | (2006.01) |
| C12N 9/42 | (2006.01) |

(52) U.S. Cl.
CPC .............. *C12N 1/14* (2013.01); *C07K 14/38* (2013.01); *C12N 9/24* (2013.01); *C12N 9/2437* (2013.01); *C12N 9/485* (2013.01); *C12N 9/62* (2013.01); *C12Y 302/01091* (2013.01)

(58) Field of Classification Search
None
See application file for complete search history.

(56) References Cited

FOREIGN PATENT DOCUMENTS

| | | |
|---|---|---|
| WO | 00/46375 | 8/2000 |
| WO | 01/68864 | 9/2001 |
| WO | 2012/001169 | 1/2012 |

OTHER PUBLICATIONS

Yoon, et al. "Disruption of ten protease genes in the filamentous fungus Aspergillus oryzae highly improves production of heterologous proteins", Appl Microbiol Biotechnol (2011) 89:747-759.
European Search Report dated Jun. 30, 2016, 8 pages.

*Primary Examiner* — Jim Ketter
(74) *Attorney, Agent, or Firm* — Rankin, Hill & Clark LLP (57) ABSTRACT

Provided are an *Aspergillus* mutant strain which can dramatically enhance production of a heterologous enzyme when a saccharifying enzyme gene is transferred into the strain to perform transformation and a transformant having a saccharifying enzyme gene transferred into the *Aspergillus* mutant strain. The *Aspergillus* mutant strain has been completely or partially deficient in three genes of *Aspergillus oryzae* strain HO2 (accession number: NITE BP-01750): a prtR gene coding for a transcription factor; a pepA gene coding for an extracellular acid protease; and a cpI gene coding for an extracellular acid carboxypeptidase.

6 Claims, 1 Drawing Sheet

ASPERGILLUS MUTANT STRAIN AND TRANSFORMANT THEREOF

BACKGROUND OF THE INVENTION

Field of the Invention

The present invention relates to an *Aspergillus* mutant strain suitable for solid culture and also suitable as a host for genetic transformation and a transformant obtained from the *Aspergillus* mutant strain.

Description of the Related Art

Conventionally, a method for manufacturing alcohol such as ethanol by saccharizing lignocellulosic biomass, such as rice straw and corn stover, as a substrate using a saccharifying enzyme and fermenting the resulting sugars by microorganisms (alcohol-fermenting microorganisms) is known.

It is known that transformants into which a saccharifying enzyme gene has been introduced into *Aspergillus* strains such as *Aspergillus oryzae* are used when the lignocellulosic biomass is saccharized with a saccharifying enzyme. For example, the transformants are solid cultured by using the lignocellulosic biomass to produce the saccharifying enzyme, so that the lignocellulosic biomass is saccharized with the saccharifying enzyme.

However, because *Aspergillus oryzae* has protease genes and produces proteases, it has a problem in that a heterologous enzyme produced by the transformant may be degraded by the proteases.

To solve the problem, it is known that deletion of protease genes of *Aspergillus oryzae* will enhance production of the heterologous enzyme (see e.g., Disruption of ten protease genes in the filamentous fungus *Aspergillus oryzae* highly improves production of heterologous proteins, Appl Microbiol Biotechnol (2011) 89: 747-759).

However, an *Aspergillus oryzae* deficient in one or more protease genes cannot sufficiently enhance production of the heterologous enzyme. Therefore, further improvements are desired.

SUMMARY OF THE INVENTION

In light of such a problem, the object of the present invention is to provide an *Aspergillus* mutant strain which can dramatically enhance production of a heterologous enzyme when a saccharifying enzyme gene is transferred into the strain to perform transformation and a transformant in which a saccharifying enzyme gene has been transferred into the *Aspergillus* mutant strain.

To achieve such an object, the *Aspergillus* mutant strain of the present invention is characterized in that it has been completely or partially deficient in each of three genes of prtR gene coding for a transcription factor, pepA gene coding for an extracellular acid protease, and cpI gene coding for an extracellular acid carboxypeptidase from *Aspergillus oryzae* strain HO2 (accession number: NITE BP-01750).

According to the *Aspergillus* mutant strain of the present invention, complete or partial deletion of the prtR gene makes it unable to express a transcription factor that positively controls expression of protease genes, suppressing expression of a plurality of protease genes. According to the *Aspergillus* mutant strain of the present invention, complete or partial deletion of the pepA gene will suppress expression of the extracellular acid protease gene. According to the *Aspergillus* mutant strain of the present invention, complete or partial deletion of the cpI gene will suppress expression of the extracellular acid carboxypeptidase gene.

Therefore, when a saccharifying enzyme gene is transferred into the *Aspergillus* mutant strain of the present invention to obtain a transformant, the transformant can reduce degradation of the saccharifying enzyme (heterologous enzyme), which is produced from the transformant, with a plurality of proteases including an extracellular acid protease and an extracellular acid carboxypeptidase, thereby dramatically enhancing production of the saccharifying enzyme.

The *Aspergillus* mutant strain of the present invention is preferably *Aspergillus oryzae* strain HO4 (accession number: NITE BP-01980) for producing the transformant.

The transformant of the present invention is characterized in that a saccharifying enzyme gene is transferred into an *Aspergillus* mutant strain completely or partially deficient in each of three genes of prtR gene coding for a transcription factor, pepA gene coding for an extracellular acid protease, and cpI gene coding for an extracellular acid carboxypeptidase of *Aspergillus oryzae* strain HO2 (accession number: NITE BP-01750).

According to the transformant of the present invention, complete or partial deletion of the prtR gene, pepA gene, and cpI gene will suppress expression of a plurality of protease genes including an extracellular acid protease gene and an extracellular acid carboxypeptidase gene. The transformant of the present invention can reduce degradation of the saccharifying enzyme (heterologous enzyme) produced by the transferred saccharifying enzyme gene with a plurality of proteases including an extracellular acid protease and an extracellular acid carboxypeptidase, thereby dramatically enhancing production of the saccharifying enzyme.

In the transformant of the present invention, the saccharifying enzyme gene is preferably at least one gene selected from a group consisting of a cellobiohydrolase gene, a β-glucosidase gene, an endoxylanase gene, an arabinofuranosidase gene, a glucuronidase gene, and an endoglucanase gene.

More specifically, the saccharifying enzyme gene is preferably at least one gene selected from a group consisting of a cellobiohydrolase gene from *Acremonium cellulolyticus*, a β-glucosidase gene from *Acremonium cellulolyticus*, an endoxylanase gene from a strain of genus *Thermoascus*, an arabinofuranosidase gene from *Acremonium cellulolyticus*, and a glucuronidase gene from *Acremonium cellulolyticus*.

In the transformant of the present invention, it is preferable that the saccharifying enzyme gene is introduced into chromosome.

DETAILED DESCRIPTION OF THE PREFERRED EMBODIMENTS

Embodiments of the present invention will now be described in more detail with reference to the accompanying drawing.

The *Aspergillus* mutant strain of the present embodiment has been completely or partially deficient in each of the three genes of prtR gene coding for a transcription factor, pepA gene coding for an extracellular acid protease, and cpI gene coding for an extracellular acid carboxypeptidase from *Aspergillus oryzae* strain HO2.

*Aspergillus oryzae* strain HO2 is a mutant strain that has been further deficient in ligD gene from *Aspergillus oryzae* strain HO1 which is a uridine auxotrophic mutant completely or partially deficient in pyrG gene from *Aspergillus oryzae* strain AOK27L (available from AKITA KONNO CO., LTD.).

*Aspergillus oryzae* strain HO1 and *Aspergillus oryzae* strain HO2 are deposited by the applicant to the National Institute of Technology and Evaluation Patent Microorganisms Depository (2-5-8-122 Kazusakamatari, Kisarazu-shi, Chiba, Japan) on Nov. 12, 2013. The accession numbers of *Aspergillus oryzae* strain HO1 and *Aspergillus oryzae* strain HO2 are NITE BP-01749 and NITE BP-01750, respectively.

A method for completely or partially deleting each of the three genes of prtR gene, pepA gene, and cpI gene from *Aspergillus oryzae* strain HO2 can be properly selected and used from known techniques used in genetic transformation of microorganisms such as protoplast-PEG method and spontaneous mutation.

The applicant named the *Aspergillus* mutant strain completely or partially deficient in all three gene of prtR gene, pepA gene, and cpI gene from *Aspergillus oryzae* strain HO2 as *Aspergillus oryzae* strain HO4 and deposited it to the National Institute of Technology and Evaluation Patent Microorganisms Depository (2-5-8-122 Kazusakamatari, Kisarazu-shi, Chiba, Japan) on Dec. 9, 2014 (accession number: NITE BP-01980).

The saccharifying enzyme gene of the transformant of the present embodiment is chromosomally integrated in *Aspergillus oryzae* strain HO4.

The saccharifying enzyme gene is at least one gene selected from the group consisting of, for example, a cellobiohydrolase gene, a β-glucosidase gene, an endoxylanase gene, an arabinofuranosidase gene, a glucuronidase gene, and an endoglucanase gene.

More specifically, the saccharifying enzyme gene is at least one gene selected from the group consisting of a cellobiohydrolase gene from *Acremonium cellulolyticus*, a β-glucosidase gene from *Acremonium cellulolyticus*, an endoxylanase gene from a strain of genus *Thermoascus*, an arabinofuranosidase gene from *Acremonium cellulolyticus*, and a glucuronidase gene from *Acremonium cellulolyticus*.

The transformant can be obtained by chromosomally integrating the expression vector including an expression cassette for expressing the saccharifying enzyme gene in *Aspergillus oryzae* strain HO4. The expression cassette is a combination of DNA which is required for expressing a structural gene and contains a promoter and a terminator which function with the structural gene in a host cell. The expression cassette may further contain either or both of 5'-untranslated region and 3'-untranslated region.

As expression vectors including the expression cassette, optionally modified vectors properly selected from known vectors available for transformation of *Aspergillus* strains including *Aspergillus oryzae* can be used.

A transformation method of chromosomally integrating an expression vector in *Aspergillus oryzae* strain HO4 is not particularly limited but various methods available for gene transfer into *Aspergillus* strains including *Aspergillus oryzae* can be performed. The transformation method can include, for example, protoplast-PEG method, PEG-calcium method (Mol. Gen. Genet., vol. 218, p. 99-104(1989)), electroporation method, and *Agrobacterium* method or the like.

According to the transformant of the present embodiment, complete or partial deletion of each of the three genes of prtR gene, pepA gene, and cpI gene will suppress expression of a plurality of protease genes including an extracellular acid protease gene and an extracellular acid carboxypeptidase gene. Therefore, the transformant of the present embodiment can reduce degradation of the saccharifying enzyme (heterologous enzyme) produced by the introduced saccharifying enzyme gene, with a plurality of proteases including an extracellular acid protease and an extracellular acid carboxypeptidase, thereby dramatically enhancing production of the saccharifying enzyme.

Examples and Comparative Examples of the present invention will be now described.

Example 1

In this Example, *Aspergillus oryzae* strain HO4, which is an *Aspergillus* mutant strain deficient in three genes of prtR gene, pepA gene, and cpI gene, was constructed from *Aspergillus oryzae* strain HO2 as follows.

The first *Aspergillus* mutant strain deficient in prtR gene was constructed from *Aspergillus oryzae* strain HO2 as follows.

A total of four gene fragments were obtained by PCR amplification and purification as described below. In the PCR amplification where a DNA polymerase (manufactured by TOYOBO CO., LTD., product name: KOD FX neo) was utilized, primers 1 and 2; primers 3 and 4; and primers 5 and 6 were used to amplify the upstream sequence of prtR gene, the downstream sequence of prtR gene, and the sequence for marker recycling, respectively, with genomic DNA from *Aspergillus oryzae* strain HO2 as a template, and primers 7 and 8 were used to amplify the pyrG gene expression cassette with genomic DNA from *Aspergillus awamori* strain HA1 (accession number: NITE BP-01751) as a template. In the purification, a purification kit (manufactured by QIAGEN, product name: QIAquick PCR purification kit) was utilized.

A plasmid pRI910 (manufactured by Takara Bio Inc.) was then treated with the restriction enzyme SmaI (manufactured by Takara Bio Inc.) at 30° C. and purified using the above-mentioned purification kit to obtain a linearized plasmid (hereinafter referred to as "the first linearized plasmid").

Three gene fragments of the upstream sequence, the pyrG gene expression cassette, and the first linearized plasmid were then transformed into an *E. coli* strain HST08 (obtained from Takara Bio Inc.) using the cloning kit (manufactured by Takara Bio Inc., product name: In-Fusion (R) HD Cloning Kit) to obtain a plasmid pRI-AoΔprtR1::pyrG in which the upstream sequence and the pyrG gene expression cassette are inserted at a SmaI site of plasmid pRI910.

The plasmid pRI-AoΔprtR1::pyrG was then treated with the restriction enzyme NotI (manufactured by Takara Bio Inc.) at 37° C. and purified using the above-mentioned purification kit to obtain a linearized plasmid pRI-AoΔprtR1::pyrG (hereinafter referred to as "the second linearized plasmid").

Three gene fragments of the sequence for marker recycling, the downstream sequence, the second linearized plasmid were then transformed into an *E. coli* strain HST08 using the above-mentioned cloning kit to obtain a plasmid pRI-AoΔprtR::pyrGR in which the sequence for marker recycling and the downstream sequence are inserted downstream of the pyrG gene expression cassette in the plasmid pRI-AoΔprtR1::pyrG.

The plasmid pRI-AoΔprtR::pyrGR was then used as a template to perform PCR amplification in which primers 9 and 10 were utilized with the above-mentioned DNA polymerase and the amplified products were purified using the above-mentioned purification kit to obtain a gene fragment for transformation of *Aspergillus* strains.

According to the conventional method of PEG-calcium method, the gene fragment for transformation of *Aspergillus* strains was then used to transform *Aspergillus oryzae* strain HO2.

The transformed *Aspergillus oryzae* strain HO2 was then selected for survival in the CD culture medium to obtain prtR gene deletion strains.

The spore suspension from the resulting prtR gene deletion strains was then inoculated at $1 \times 10^6$ spores/plate onto CD plate media containing 5-fluoroorotic acid monohydrate (manufactured by Wako Pure Chemical Industries, Ltd.) in final concentration of 1 mg/mL and uridine (manufactured by Sigma-Aldrich Corporation) in final concentration of 20 mM. A viable strain was selected to obtain the first *Aspergillus* mutant strain which is a prtR gene deletion strain from *Aspergillus oryzae* strain HO2 and is auxotrophic for uridine.

The base sequences of primers 1-10 are shown in Table 1.

TABLE 1

| Primer number | Base sequence 5'→3' | SEQ ID NO. | Note |
|---|---|---|---|
| 1 | tcgagctcgg tacccgcgcc ttgttcctta aagggtctaa tg | 1 | prtR gene upstream sequence |
| 2 | gatgctcgag cttgcgaata atcggcgagt agaacaagct gag | 2 | prtR gene upstream sequence |
| 3 | tttacatggt ctggcgcgtg attg | 3 | prtR gene downstream sequence |
| 4 | aggatccccg cggcctcaac gacggaatcc ccatcatcta c | 4 | prtR gene downstream sequence |
| 5 | gatgattagg cggccgggta tgcccgatca caatcttcaa c | 5 | Sequence for marker recycling |
| 6 | gccagaccat gtaaagcggc cgcgaataat cggcgagtag aacaagctga g | 6 | Sequence for marker recycling |
| 7 | gcaagctcga gcatccaact aaactag | 7 | pyrG gene expression cassette |
| 8 | ctctagagga tccccgcggc cgcctaatca tcctgcagct ccgtcattg | 8 | pyrG gene expression cassette |
| 9 | ctcatgatcc tggcacgaca g | 9 | Gene fragment for transformation of *Aspergillus* strains |
| 10 | cgggaaacga caatctgatc ctg | 10 | Gene fragment for transformation of *Aspergillus* strains |

The second *Aspergillus* mutant strain further deficient in pepA gene was then constructed from the first *Aspergillus* mutant strain as follows.

A total of four gene fragments were obtained by PCR amplification and purification as described below. In the PCR amplification where a DNA polymerase (manufactured by TOYOBO CO., LTD., product name: KOD-plus-neo) was utilized, primers 11 and 12; primers 13 and 14; and primers 15 and 16 were used to amplify the upstream sequence of pepA gene, the downstream sequence of pepA gene, and the sequence for marker recycling, respectively, with genomic DNA from *Aspergillus oryzae* strain HO2 as a template, and primers 7 and 8 were used to amplify the pyrG gene expression cassette with genomic DNA from *Aspergillus awamori* strain HA1 (accession number: NITE BP-01751) as a template. In the purification, a purification kit (manufactured by QIAGEN, product name: QIAquick PCR purification kit) was utilized.

The first *Aspergillus* mutant strain was then transformed in the very same manner as the transformation of *Aspergillus oryzae* strain HO2 except that the above-mentioned four gene fragments were used.

The transformed first *Aspergillus* mutant strain was then selected for survival in the CD culture medium to obtain pepA gene deletion strains.

The second *Aspergillus* mutant strain which is a prtR-pepA double gene deletion strain from *Aspergillus oryzae* strain HO2 and is auxotrophic for uridine was then obtained in the same manner as the first *Aspergillus* mutant strain was obtained from the *Aspergillus oryzae* strain HO2 except that the spore suspension of the resulting pepA gene deletion strains was used.

The base sequences of primers 11-16 are shown in Table 2.

TABLE 2

| Primer number | Base sequence 5'→3' | SEQ ID NO. | Note |
|---|---|---|---|
| 11 | tcgagctcgg tacccgctaa gtggagagcg accaaaatca g | 11 | pepA gene upstream sequence |
| 12 | gatgctcgag cttgcagtga ttgctctcta gacgaaatgt ggag | 12 | pepA gene upstream sequence |
| 13 | ctgatgcacg gcctaagtct aatgaac | 13 | pepA gene downstream sequence |
| 14 | aggatccccg cggcccgcca tccgtgtacc acaactac | 14 | pepA gene downstream sequence |
| 15 | gatgattagg cggcctgata tggaggtgga gatcagcaga ac | 15 | Sequence for marker recycling |
| 16 | taggccgtgc atcaggcggc cgcagtgatt gctctctaga cgaaatgtgg ag | 16 | Sequence for marker recycling |

*Aspergillus oryzae* strain HO4 which is an *Aspergillus* mutant strain further deficient in cpI gene was then constructed from the second *Aspergillus* mutant strain as follows.

A total of four gene fragments were obtained by PCR amplification and purification as described below. In the PCR amplification where a DNA polymerase (manufactured by TOYOBO CO., LTD., product name: KOD-plus-neo) was utilized, primers 17 and 18; primers 19 and 20; and primers 21 and 22 were used to amplify the upstream sequence of cpI gene, the downstream sequence of cpI gene, and the sequence for marker recycling, respectively, with genomic DNA from *Aspergillus oryzae* strain HO2 as a template, and primers 7 and 8 were used to amplify the pyrG gene expression cassette with genomic DNA from *Aspergillus awamori* strain HA1 (accession number: NITE BP-01751) as a template. In the purification, a purification kit (manufactured by QIAGEN, product name: QIAquick PCR purification kit) was utilized.

The second *Aspergillus* mutant strains were then transformed in the very same manner as the transformation of *Aspergillus oryzae* strain HO2 except that the above-mentioned four gene fragments were used.

The transformed second *Aspergillus* mutant strain was then selected for survival in the CD culture medium to obtain cpI gene deletion strains.

*Aspergillus oryzae* strain HO4, as an *Aspergillus* mutant strain, which is a prtR-pepA-cpI triple gene deletion strain from *Aspergillus oryzae* strain HO2 and is auxotrophic for uridine was then obtained in the same manner as the first *Aspergillus* mutant strain was obtained from the *Aspergillus oryzae* strain HO2 except that the spore suspension of the resulting cpI gene deletion strains was used.

The base sequences of primers 17-22 are shown in Table 3.

TABLE 3

| Primer number | Base sequence 5'→3' | SEQ ID NO. | Note |
|---|---|---|---|
| 17 | tcgagctcgg tacccggtat gtacaggatg gcgcatcatg | 17 | cpI gene upstream sequence |
| 18 | gatgctcgag cttgcgttta caagtgcagt ccacttctgg ttc | 18 | cpI gene upstream sequence |
| 19 | cacatgacga gacggttgaa acaatatgac | 19 | cpI gene downstream sequence |
| 20 | aggatccccg cggccggacc gttcacgtgt cattgtcatg | 20 | cpI gene downstream sequence |
| 21 | gatgattagg cggcctcatc ttgccgatcc tctccattct g | 21 | Sequence for marker recycling |
| 22 | ccgtctcgtc atgtggcggc cgcgtttaca agtgcagtcc acttctggtt c | 22 | Sequence for marker recycling |

Comparative Example 1

In this Comparative Example, the third *Aspergillus* mutant strain deficient in three genes of prtR gene, pepA gene, and tppA gene was constructed from *Aspergillus oryzae* strain HO2 as follows.

The second *Aspergillus* mutant strain deficient in two genes of prtR gene and pepA gene from *Aspergillus oryzae* strain HO2 was obtained in the same manner as Example 1. The third *Aspergillus* mutant strain further deficient in tppA gene was then constructed from the second *Aspergillus* mutant strain as follows.

A total of four gene fragments were obtained by PCR amplification and purification as described below. In the PCR amplification where a DNA polymerase (manufactured by TOYOBO CO., LTD., product name: KOD-plus-neo) was utilized, primers 23 and 24; primers 25 and 26; and primers 27 and 28 were used to amplify the upstream sequence of tppA gene, the downstream sequence of tppA gene, and the sequence for marker recycling, respectively, with genomic DNA from *Aspergillus oryzae* strain HO2 as a template, and primers 7 and 8 were used to amplify the pyrG gene expression cassette with genomic DNA from *Aspergillus awamori* strain HA1 (accession number: NITE BP-01751) as a template. In the purification, a purification kit (manufactured by QIAGEN, product name: QIAquick PCR purification kit) was utilized.

The second *Aspergillus* mutant strain was then transformed in the same manner as the first *Aspergillus* mutant strain was obtained from *Aspergillus oryzae* strain HO2 except that the above-mentioned four gene fragments were used.

The transformed second *Aspergillus* mutant strain was then selected for survival in the CD culture medium to obtain tppA gene deletion strains.

The third *Aspergillus* mutant strain which is a prtR-pepA-tppA triple gene deletion strain from *Aspergillus oryzae* strain HO2 and is auxotrophic for uridine was then obtained in the same manner as the first *Aspergillus* mutant strain was obtained from the *Aspergillus oryzae* strain HO2 except that the spore suspension of the resulting tppA gene deletion strains was used.

The base sequences of primers 23-28 are shown in Table 4.

TABLE 4

| Primer number | Base sequence 5'→3' | SEQ ID NO. | Note |
|---|---|---|---|
| 23 | tcgagctcgg taccccctgga ccaaccgcca aggttag | 23 | tppA gene upstream sequence |
| 24 | gatgctcgag cttgcactga attgcaatta atggcggaca atg | 24 | tppA gene upstream sequence |
| 25 | gtgtcttaga tgcgactcaa tacaactgtt c | 25 | tppA gene downstream sequence |
| 26 | aggatccccg cggccttgag gctgaagact taaatacgac attgc | 26 | tppA gene downstream sequence |
| 27 | gatgattagg cggcccgtgc aaaccaagca aacaagcatc | 27 | Sequence for marker recycling |
| 28 | tcgcatctaa gacacgcggc cgcactgaat tgcaattaat ggcggacaat g | 28 | Sequence for marker recycling |

Comparative Example 2

In this Comparative Example, the fourth *Aspergillus* mutant strain deficient in three genes of prtR gene, cpI gene, and tppA gene was constructed from *Aspergillus oryzae* strain HO2 as follows.

The first *Aspergillus* mutant strain deficient in prtR gene was obtained from *Aspergillus oryzae* strain HO2 in the same manner as Example 1. The fifth *Aspergillus* mutant strain further deficient in cpI gene was then obtained from the first *Aspergillus* mutant strain in the same manner as Example 1 except that the first *Aspergillus* mutant strain was used in place of the second *Aspergillus* mutant strain.

The fourth *Aspergillus* mutant strain further deficient in tppA gene was then obtained from the fifth *Aspergillus* mutant strain in the same manner as Comparative Example 1 except that the fifth *Aspergillus* mutant strain was used in place of the second *Aspergillus* mutant strain.

The fourth *Aspergillus* mutant strain is an *Aspergillus* mutant strain which is prtR-cpI-tppA triple gene deletion strain from *Aspergillus oryzae* strain HO2 and is auxotrophic for uridine.

Comparative Example 3

In this Comparative Example, the sixth *Aspergillus* mutant strain deficient in four genes of prtR gene, pepA gene, cpI gene, and tppA gene was constructed from *Aspergillus oryzae* strain HO2 as follows.

*Aspergillus oryzae* strain HO4 as an *Aspergillus* mutant strain deficient in three genes of prtR gene, pepA gene, and cpI gene from *Aspergillus oryzae* strain HO2 was obtained in the same manner as Example 1.

The sixth *Aspergillus* mutant strain further deficient in tppA gene was then obtained from *Aspergillus oryzae* strain HO4 in the same manner as Comparative Example 1 except that *Aspergillus oryzae* strain HO4 was used in place of the second *Aspergillus* mutant strain.

The sixth *Aspergillus* mutant strain is an *Aspergillus* mutant strain which is a prtR-pepA-cpI-tppA quadruplex gene deletion strain from *Aspergillus oryzae* strain HO2 and is auxotrophic for uridine.

[Construction of Transformants]

A method of constructing transformants will be now described by illustrating the transfer of a cellobiohydrolase (cbh1) gene.

A total of six gene fragments were obtained by PCR amplification and purification as described below. In the PCR amplification where a DNA polymerase (manufactured by TOYOBO CO., LTD., product name: KOD-plus-neo) was utilized, primers 29 and 30; primers 31 and 32; primers 33 and 34; and primers 35 and 36 were used to amplify the upstream sequence of pyrG gene, the downstream sequence of pyrG gene, tef1 promoter gene, and agdA terminator gene, respectively, with genomic DNA from *Aspergillus oryzae* strain HO2 as a template, primers 37 and 38 were used to amplify a cellobiohydrolase (cbh1) gene with genomic DNA from *Acremonium cellulolyticus* strain H1 (accession number: NITE BP-11508) as a template, and primers 39 and 40 were used to amplify the pyrG gene expression cassette with genomic DNA from *Aspergillus awamori* strain HA1 (accession number: NITE BP-01751) as a template. In the purification, a purification kit (manufactured by QIAGEN, product name: QIAquick PCR purification kit) was utilized.

A plasmid pMD20 (manufactured by Takara Bio Inc.) was then treated with the restriction enzyme SmaI (manufactured by Takara Bio Inc.) at 30° C. and purified using the above-mentioned purification kit to obtain plasmid restriction products (gene fragments).

Each of the gene fragments thus obtained was sequentially transformed into an *E. coli* strain HST08 (manufactured by Takara Bio Inc.) using a cloning kit (manufactured by Takara Bio Inc., product name: In-Fusion (R) HD Cloning Kit) to obtain a plasmid pPPT1-CBH1.

The resulting plasmid pPPT1-CBH1 was then used as a template to perform PCR amplification in which primers 41 and 42 were utilized with the above-mentioned DNA polymerase and the amplified products were purified using the above-mentioned purification kit to obtain a gene fragment for transformation of *Aspergillus* strains (pyrG-CBH1 fragment).

According to the conventional method of PEG-calcium method, the gene fragment for transformation of *Aspergillus* strains (pyrG-CBH1 fragment) was then used to transform *Aspergillus oryzae* strain HO2 (Reference Example), *Aspergillus oryzae* strain HO4 (Example 1), the third *Aspergillus* mutant strain (Comparative Example 1), the fourth *Aspergillus* mutant strain (Comparative Example 2), and the sixth *Aspergillus* mutant strain (Comparative Example 3) to obtain respective transformants.

The resulting transformants were then selected for survival on the CD plate media to obtain the respective transformants corresponding to Reference Example, Example 1, and Comparative Examples 1-3. The transformants can produce a cellobiohydrolase (cbh1) because the cellobiohydrolase gene is chromosomally integrated in the transformants. The transformant into which a cellobiohydrolase (cbh1) gene was transferred and which can produce a cellobiohydrolase is referred to as "CBH1-producing strain" hereinafter.

The base sequences of primers 29-42 are shown in Table 5.

TABLE 5

| Primer number | Base sequence 5'→3' | SEQ ID NO. | Note |
|---|---|---|---|
| 29 | ggatatcgga tccccccaga ggtgacttta tccaagattc cttc | 29 | pyrG gene upstream sequence |
| 30 | caattgccgc gaaaaattaa attgaatcta tg | 30 | pyrG gene upstream sequence |
| 31 | ttttcgcggc aattgcccgg ggtagtggtg gatacgtact cctttttatgg | 31 | pyrG gene downstream sequence |
| 32 | tcgagctcgg tacccttcag gtcacgttct aagcttatca gctg | 32 | pyrG gene downstream sequence |
| 33 | ctaatcatcc tgcagctccg tcattg | 33 | tef1 promoter gene |
| 34 | tcgcggcaat tgcccgcaag ctcgagcatc caactaaact ag | 34 | tef1 promoter gene |
| 35 | ccaccactac cccgggaagc gtaacaggat agcctagacc | 35 | agdA terminator gene |
| 36 | ctgcaggatg attagagtaa cccattcccg gttctctagc tg | 36 | agdA terminator gene |
| 37 | atgtctgcct tgaactcttt caatatgtac aag | 37 | Cellobio-hydrolase gene |
| 38 | atcctgttac gcttcctaca aacattgaga gtagtaaggg ttcacg | 38 | Cellobio-hydrolase gene |
| 39 | atccaccact accccgtaag gtccgagaca gtaagggatt g | 39 | pyrG gene expression cassette |
| 40 | gttcaaggca gacattttga aggtggtgcg aactttgtag ttc | 40 | pyrG gene expression cassette |

TABLE 5-continued

| Primer number | Base sequence 5'→3' | SEQ ID NO. | Note |
|---|---|---|---|
| 41 | cagtgagcgc aacgcaatta atgtgagtta g | 41 | Gene fragment for transformation of *Aspergillus* strains |
| 42 | gggatgtgct gcaaggcgat taagttg | 42 | Gene fragment for transformation of *Aspergillus* strains |

[Measurement of Cellobiohydrolase Production]

A method of measuring cellobiohydrolase production from respective CBH1-producing strains corresponding to *Aspergillus* mutant strains of Reference Example, Example 1, and Comparative Examples 1-3 will now be described.

To measure cellobiohydrolase production from the CBH1-producing strains, each of the CBH1-producing strains was cultured on the CD plate media for a week to form spores and collected using 0.01% POLYSORBATE 20 (manufactured by Wako Pure Chemical Industries, Ltd.) to obtain spore suspension.

A 100 mL Erlenmeyer flask was charged with 30 mL of PD liquid medium (2 (w/v) % dextrin, 1 (w/v) % polypeptone, 0.1 (w/v) % casamino acids, 0.5 (w/v) % monobasic potassium phosphate, 0.05 (w/v) % magnesium sulfate, and 0.1 (w/v) % sodium nitrate). The spore was inoculated to the flask at the final concentration of $1 \times 10^4$ spores/mL and liquid-cultured at 30° C. for 6 days to obtain cultures of CBH1-producing strains that secreted and provided cellobiohydrolase (CBH1), which is the enzyme of interest, into the liquid culture medium.

CBH1 concentration in each liquid culture was then confirmed by SDS-PAGE analysis. 0.25 μg, 0.5 μg, and 2 μg of BSA were run simultaneously as a standard of protein concentration. CBH1 concentration in 10 μL of enzyme sample was calculated from image analysis using ChemiDoc (R) XRS+ system.

Figure 1:
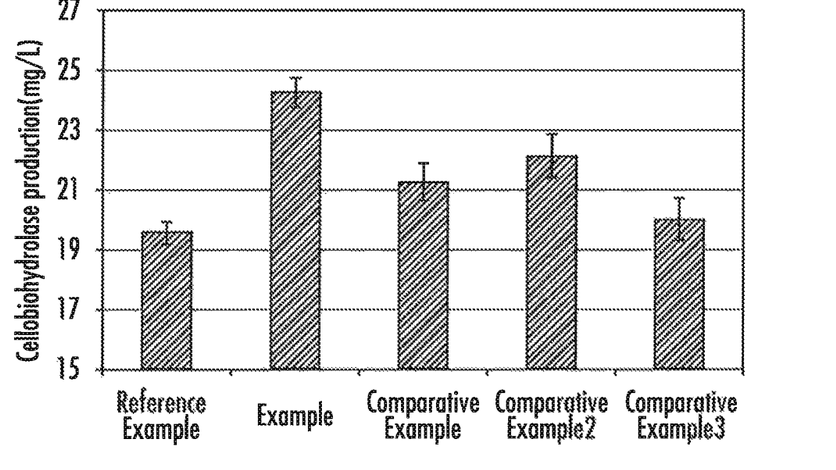
FIG. 1 is a graph showing the production amount of a saccharifying enzyme in the transformant of the *Aspergillus* mutant strain of the present invention and transformants of other *Aspergillus* mutant strains.

The results are shown in FIG. 1 and Table 6.

TABLE 6

| | CBH1 Production (mg/L) | Relative value |
|---|---|---|
| Reference Example | 19.54 | 1.0 |
| Example 1 | 24.23 | 1.24 |
| Comparative Example 1 | 21.30 | 1.09 |
| Comparative Example 2 | 22.08 | 1.13 |
| Comparative Example 3 | 19.93 | 1.02 |

As shown in FIG. 1 and Table 6, the relative value of cellobiohydrolase (CBH1) production of the transformant of *Aspergillus oryzae* strain HO4 (Example 1) deficient in three genes of prtR gene coding for a transcription factor, pepA gene coding for an extracellular acid protease, and cpI gene coding for an extracellular acid carboxypeptidase from *Aspergillus oryzae* strain HO2 is 1.24 if the relative value of CBH1 production of the transformant of *Aspergillus oryzae* strain HO2 (Reference Example) is considered as 1.0. It is clear that the transformant of Example 1 is greatly superior to the transformant of Reference Example.

FIG. 1 and Table 6 also reveal that the relative values of CBH1 production of transformants of the third *Aspergillus* mutant strain (Comparative Example 1) deficient in prtR gene, pepA gene, and tppA gene from *Aspergillus oryzae* strain HO2, of the fourth *Aspergillus* mutant strain (Comparative Example 2) deficient in prtR gene, cpI gene, and tppA gene, and of the sixth *Aspergillus* mutant strain (Comparative Example 3) deficient in prtR gene, pepA gene, cpI gene, and tppA gene ranged from 1.02 to 1.13 and all the strains are inferior to the transformant of Example 1.

Therefore, it is obvious that the transformants of *Aspergillus oryzae* strain HO4 in Example 1 can dramatically enhance production of a saccharifying enzyme CBH1.

What is claimed is:

1. An *Aspergillus* mutant strain wherein the mutant strain is completely or partially deficient in three genes of *Aspergillus oryzae* strain HO2 (accession number: NITE BP-01750): a prtR gene coding for a transcription factor; a pepA gene coding for an extracellular acid protease; and a cpI gene coding for an extracellular acid carboxypeptidase.

2. The *Aspergillus* mutant strain according to claim 1, wherein the mutant strain is *Aspergillus oryzae* strain HO4 (accession number: NITE BP-01980).

3. A transformant wherein the transformant is constructed by transferring a saccharifying enzyme gene into an *Aspergillus* mutant strain completely or partially deficient in three genes of *Aspergillus oryzae* strain HO2 (accession number: NITE BP-01750): a prtR gene coding for a transcription factor; a pepA gene coding for an extracellular acid protease; and a cpI gene coding for an extracellular acid carboxypeptidase.

4. The transformant according to claim 3, wherein the saccharifying enzyme gene is at least one gene selected from a group consisting of a cellobiohydrolase gene, a β-glucosidase gene, an endoxylanase gene, an arabinofuranosidase gene, a glucuronidase gene, and an endoglucanase gene.

5. The transformant according to claim 4, wherein the saccharifying enzyme gene is at least one gene selected from a group consisting of a cellobiohydrolase gene from *Acremonium cellulolyticus*, a β-glucosidase gene from *Acremonium cellulolyticus*, an endoxylanase gene from a strain of genus *Thermoascus*, an arabinofuranosidase gene from *Acremonium cellulolyticus*, and a glucuronidase gene from *Acremonium cellulolyticus*.

6. The transformant according to claim 3, wherein the saccharifying enzyme gene is chromosomally integrated.

* * * * *

SEQUENCE LISTING

```
<160> NUMBER OF SEQ ID NOS: 42

<210> SEQ ID NO 1
<211> LENGTH: 42
<212> TYPE: DNA
<213> ORGANISM: Aspergillus oryzae

<400> SEQUENCE: 1
tcgagctcgg tacccgcgcc ttgttcctta aagggtctaa tg                    42

<210> SEQ ID NO 2
<211> LENGTH: 43
<212> TYPE: DNA
<213> ORGANISM: Aspergillus oryzae

<400> SEQUENCE: 2
gatgctcgag cttgcgaata atcggcgagt agaacaagct gag                   43

<210> SEQ ID NO 3
<211> LENGTH: 24
<212> TYPE: DNA
<213> ORGANISM: Aspergillus oryzae

<400> SEQUENCE: 3
```

```
tttacatggt ctggcgcgtg attg                                          24

<210> SEQ ID NO 4
<211> LENGTH: 41
<212> TYPE: DNA
<213> ORGANISM: Aspergillus oryzae

<400> SEQUENCE: 4 aggatcccccg cggcctcaac gacggaatcc ccatcatcta c                      41

<210> SEQ ID NO 5
<211> LENGTH: 41
<212> TYPE: DNA
<213> ORGANISM: Aspergillus oryzae

<400> SEQUENCE: 5
gatgattagg cggccgggta tgcccgatca caatcttcaa c                       41

<210> SEQ ID NO 6
<211> LENGTH: 51
<212> TYPE: DNA
<213> ORGANISM: Aspergillus oryzae

<400> SEQUENCE: 6
gccagaccat gtaaagcggc cgcgaataat cggcgagtag aacaagctga g            51

<210> SEQ ID NO 7
<211> LENGTH: 27
<212> TYPE: DNA
<213> ORGANISM: Aspergillus awamori

<400> SEQUENCE: 7
gcaagctcga gcatccaact aaactag                                       27

<210> SEQ ID NO 8
<211> LENGTH: 49
<212> TYPE: DNA
<213> ORGANISM: Aspergillus awamori

<400> SEQUENCE: 8
ctctagagga tccccgcggc cgcctaatca tcctgcagct ccgtcattg               49

<210> SEQ ID NO 9
<211> LENGTH: 21
<212> TYPE: DNA
<213> ORGANISM: Rhizobium rhizogenes

<400> SEQUENCE: 9
ctcatgatcc tggcacgaca g                                             21

<210> SEQ ID NO 10
<211> LENGTH: 23
<212> TYPE: DNA
<213> ORGANISM: Rhizobium rhizogenes

<400> SEQUENCE: 10
cgggaaacga caatctgatc ctg                                           23

<210> SEQ ID NO 11
<211> LENGTH: 41
<212> TYPE: DNA
<213> ORGANISM: Aspergillus oryzae

<400> SEQUENCE: 11
```
tcgagctcgg tacccgctaa gtggagagcg accaaaatca g          41

<210> SEQ ID NO 12
<211> LENGTH: 44
<212> TYPE: DNA
<213> ORGANISM: Aspergillus oryzae

<400> SEQUENCE: 12
gatgctcgag cttgcagtga ttgctctcta gacgaaatgt ggag          44

<210> SEQ ID NO 13
<211> LENGTH: 27
<212> TYPE: DNA
<213> ORGANISM: Aspergillus oryzae

<400> SEQUENCE: 13
ctgatgcacg gcctaagtct aatgaac          27

<210> SEQ ID NO 14
<211> LENGTH: 38
<212> TYPE: DNA
<213> ORGANISM: Aspergillus oryzae

<400> SEQUENCE: 14
aggatccccg cggcccgcca tccgtgtacc acaactac          38

<210> SEQ ID NO 15
<211> LENGTH: 42
<212> TYPE: DNA
<213> ORGANISM: Aspergillus oryzae

<400> SEQUENCE: 15
gatgattagg cggcctgata tggaggtgga gatcagcaga ac          42

<210> SEQ ID NO 16
<211> LENGTH: 52
<212> TYPE: DNA
<213> ORGANISM: Aspergillus oryzae

<400> SEQUENCE: 16
taggccgtgc atcaggcggc cgcagtgatt gctctctaga cgaaatgtgg ag          52

<210> SEQ ID NO 17
<211> LENGTH: 40
<212> TYPE: DNA
<213> ORGANISM: Aspergillus oryzae

<400> SEQUENCE: 17
tcgagctcgg tacccggtat gtacaggatg gcgcatcatg          40

<210> SEQ ID NO 18
<211> LENGTH: 43
<212> TYPE: DNA
<213> ORGANISM: Aspergillus oryzae

<400> SEQUENCE: 18
gatgctcgag cttgcgttta caagtgcagt ccacttctgg ttc          43

<210> SEQ ID NO 19
<211> LENGTH: 30
<212> TYPE: DNA
<213> ORGANISM: Aspergillus oryzae

<400> SEQUENCE: 19
cacatgacga gacggttgaa acaatatgac         30

<210> SEQ ID NO 20
<211> LENGTH: 40
<212> TYPE: DNA
<213> ORGANISM: Aspergillus oryzae

<400> SEQUENCE: 20
aggatccccg cggccggacc gttcacgtgt cattgtcatg         40

<210> SEQ ID NO 21
<211> LENGTH: 41
<212> TYPE: DNA
<213> ORGANISM: Aspergillus oryzae

<400> SEQUENCE: 21
gatgattagg cggcctcatc ttgccgatcc tctccattct g         41

<210> SEQ ID NO 22
<211> LENGTH: 51
<212> TYPE: DNA
<213> ORGANISM: Aspergillus oryzae

<400> SEQUENCE: 22
ccgtctcgtc atgtggcggc cgcgtttaca agtgcagtcc acttctggtt c         51

<210> SEQ ID NO 23
<211> LENGTH: 37
<212> TYPE: DNA
<213> ORGANISM: Aspergillus oryzae

<400> SEQUENCE: 23
tcgagctcgg tacccctgga ccaaccgcca aggttag         37

<210> SEQ ID NO 24
<211> LENGTH: 43
<212> TYPE: DNA
<213> ORGANISM: Aspergillus oryzae

<400> SEQUENCE: 24
gatgctcgag cttgcactga attgcaatta atggcggaca atg         43

<210> SEQ ID NO 25
<211> LENGTH: 31
<212> TYPE: DNA
<213> ORGANISM: Aspergillus oryzae

<400> SEQUENCE: 25
gtgtcttaga tgcgactcaa tacaactgtt c         31

<210> SEQ ID NO 26
<211> LENGTH: 45
<212> TYPE: DNA
<213> ORGANISM: Aspergillus oryzae

<400> SEQUENCE: 26
aggatccccg cggccttgag gctgaagact aaatacgac attgc         45

<210> SEQ ID NO 27
<211> LENGTH: 40
<212> TYPE: DNA
<213> ORGANISM: Aspergillus oryzae

<210> SEQ ID NO 27 gatgattagg cggcccgtgc aaaccaagca aacaagcatc            40

<210> SEQ ID NO 28
<211> LENGTH: 51
<212> TYPE: DNA
<213> ORGANISM: Aspergillus oryzae

<400> SEQUENCE: 28
tcgcatctaa gacacgcggc cgcactgaat tgcaattaat ggcggacaat g    51

<210> SEQ ID NO 29
<211> LENGTH: 44
<212> TYPE: DNA
<213> ORGANISM: Aspergillus oryzae

<400> SEQUENCE: 29
ggatatcgga tcccccaga ggtgacttta tccaagattc cttc          44

<210> SEQ ID NO 30
<211> LENGTH: 32
<212> TYPE: DNA
<213> ORGANISM: Aspergillus oryzae

<400> SEQUENCE: 30
caattgccgc gaaaaattaa attgaatcta tg                    32

<210> SEQ ID NO 31
<211> LENGTH: 50
<212> TYPE: DNA
<213> ORGANISM: Aspergillus oryzae

<400> SEQUENCE: 31
ttttcgcggc aattgcccgg ggtagtggtg gatacgtact cctttatgg   50

<210> SEQ ID NO 32
<211> LENGTH: 44
<212> TYPE: DNA
<213> ORGANISM: Aspergillus oryzae

<400> SEQUENCE: 32
tcgagctcgg taccctcag gtcacgttct aagcttatca gctg         44

<210> SEQ ID NO 33
<211> LENGTH: 26
<212> TYPE: DNA
<213> ORGANISM: Aspergillus oryzae

<400> SEQUENCE: 33
ctaatcatcc tgcagctccg tcattg                           26

<210> SEQ ID NO 34
<211> LENGTH: 42
<212> TYPE: DNA
<213> ORGANISM: Aspergillus oryzae

<400> SEQUENCE: 34
tcgcggcaat gcccgcaag ctcgagcatc caactaaact ag           42

<210> SEQ ID NO 35
<211> LENGTH: 40
<212> TYPE: DNA

<213> ORGANISM: Aspergillus oryzae

<400> SEQUENCE: 35
ccaccactac cccgggaagc gtaacaggat agcctagacc    40

<210> SEQ ID NO 36
<211> LENGTH: 42
<212> TYPE: DNA
<213> ORGANISM: Aspergillus oryzae

<400> SEQUENCE: 36
ctgcaggatg attagagtaa cccattcccg gttctctagc tg    42

<210> SEQ ID NO 37
<211> LENGTH: 33
<212> TYPE: DNA
<213> ORGANISM: Acremonium cellulolyticus

<400> SEQUENCE: 37
atgtctgcct tgaactcttt caatatgtac aag    33

<210> SEQ ID NO 38
<211> LENGTH: 46
<212> TYPE: DNA
<213> ORGANISM: Acremonium cellulolyticus

<400> SEQUENCE: 38
atcctgttac gcttcctaca aacattgaga gtagtaaggg ttcacg    46

<210> SEQ ID NO 39
<211> LENGTH: 41
<212> TYPE: DNA
<213> ORGANISM: Aspergillus awamori

<400> SEQUENCE: 39
atccaccact accccgtaag gtccgagaca gtaagggatt g    41

<210> SEQ ID NO 40
<211> LENGTH: 43
<212> TYPE: DNA
<213> ORGANISM: Aspergillus awamori

<400> SEQUENCE: 40
gttcaaggca gacattttga aggtggtgcg aactttgtag ttc    43

<210> SEQ ID NO 41
<211> LENGTH: 31
<212> TYPE: DNA
<213> ORGANISM: Escherichia coli

<400> SEQUENCE: 41
cagtgagcgc aacgcaatta atgtgagtta g    31

<210> SEQ ID NO 42
<211> LENGTH: 27
<212> TYPE: DNA
<213> ORGANISM: Escherichia coli

<400> SEQUENCE: 42
gggatgtgct gcaaggcgat taagttg    27